(12) United States Patent
Jahns

(10) Patent No.: US 9,655,817 B2
(45) Date of Patent: May 23, 2017

(54) WHITENING COMPOSITION FOR TREATING THE SURFACE OF DENTAL CERAMIC AND RELATED METHODS

(71) Applicant: 3M INNOVATIVE PROPERTIES COMPANY, St. Paul, MN (US)

(72) Inventor: Michael Jahns, Düsseldorf (DE)

(*) Notice: Subject to any disclaimer, the term of this patent is extended or adjusted under 35 U.S.C. 154(b) by 28 days.

(21) Appl. No.: 14/646,277

(22) PCT Filed: Dec. 10, 2013

(86) PCT No.: PCT/US2013/074100
§ 371 (c)(1),
(2) Date: May 20, 2015

(87) PCT Pub. No.: WO2014/093329
PCT Pub. Date: Jun. 19, 2014

(65) Prior Publication Data
US 2015/0297466 A1    Oct. 22, 2015

(30) Foreign Application Priority Data
Dec. 12, 2012    (EP) .................................... 12196633

(51) Int. Cl.
*A61K 6/00* (2006.01)
*A61K 8/26* (2006.01)
(Continued)

(52) U.S. Cl.
CPC ............ *A61K 6/0094* (2013.01); *A61K 6/024* (2013.01); *A61K 8/0241* (2013.01); *A61K 8/26* (2013.01);
(Continued)

(58) Field of Classification Search
CPC .......... A61K 6/0094; A61K 8/26; A61K 8/28; A61K 8/29; A61K 8/345; A61K 8/0241;
(Continued)

(56) References Cited

U.S. PATENT DOCUMENTS 6,709,694 B1    3/2004  Suttor
6,756,421 B1    6/2004  Todo
(Continued)

FOREIGN PATENT DOCUMENTS

DE    19904522    8/2000
DE    10052203    4/2001
(Continued)

OTHER PUBLICATIONS

Arndt/Müller, Polymercharakterisierung, Hanse Verlag, 1996.
(Continued)

*Primary Examiner* — Pedro Philogene
*Assistant Examiner* — David C Comstock

(57) ABSTRACT

The invention relates to a process of treating parts of the surface of a porous dental ceramic article comprising the steps of: a) providing a composition and a porous dental ceramic article having an outer surface, b) applying the composition to only a part of the outer surface of the porous dental ceramic article, c) optionally drying the porous dental ceramic article, and d) optionally firing the porous dental ceramic article, the composition comprising: a liquid being miscible with water, but not being water, a whitening agent comprising nano-sized metal oxide particles, metal ion containing components or mixtures thereof, a stabilizer (e.g. acid, base, complexing agent or mixture thereof). the porous dental ceramic article showing a N2 adsorption and/or desorption of isotherm type IV according to IUPAC classification. The invention also relates to a dental ceramic article obtainable by a process.

15 Claims, 1 Drawing Sheet

(51) Int. Cl.
- *A61K 8/28* (2006.01)
- *A61K 8/29* (2006.01)
- *A61K 8/34* (2006.01)
- *A61Q 11/02* (2006.01)
- *A61K 8/02* (2006.01)
- *C04B 41/85* (2006.01)
- *C04B 41/00* (2006.01)
- *C04B 41/87* (2006.01)
- *C04B 41/50* (2006.01)
- *A61K 6/02* (2006.01)
- *B05D 5/06* (2006.01)
- *B05D 7/00* (2006.01)
- *C04B 111/00* (2006.01)

(52) U.S. Cl.
CPC .............. *A61K 8/28* (2013.01); *A61K 8/29* (2013.01); *A61K 8/345* (2013.01); *A61Q 11/02* (2013.01); *B05D 5/06* (2013.01); *B05D 7/00* (2013.01); *C04B 41/009* (2013.01); *C04B 41/5007* (2013.01); *C04B 41/5031* (2013.01); *C04B 41/5041* (2013.01); *C04B 41/5042* (2013.01); *C04B 41/85* (2013.01); *C04B 41/87* (2013.01); *A61K 2800/413* (2013.01); *C04B 2111/00836* (2013.01)

(58) Field of Classification Search
CPC .. A61K 6/024; A61K 2800/413; A61Q 11/02; C04B 41/85; C04B 41/87; C04B 41/009; C04B 41/5007; C04B 41/5031; C04B 41/5041; C04B 41/5042; C04B 2111/00836; B05D 5/06; B05D 7/00

USPC ............................ 433/202.1, 215, 216, 229
See application file for complete search history.

(56) References Cited

U.S. PATENT DOCUMENTS 9,365,459 B2 * 6/2016 Carden .................. A61K 6/024
2006/0117989 A1 6/2006 Hauptmann

FOREIGN PATENT DOCUMENTS

| EP | 1961719 | 8/2008 |
|---|---|---|
| WO | WO 2004-110959 | 12/2004 |
| WO | WO 2008-098157 | 8/2008 |
| WO | WO 2009-014903 | 1/2009 |
| WO | WO 2013-022612 | 2/2013 |
| WO | WO 2013-055432 | 4/2013 |

OTHER PUBLICATIONS

NAONO, "Analysis of Nitrogen Adsorption Isotherms for a Series of Porous Silicas with Uniform and Cylindrical Pores: A New Method of Calculating Pore Size Distribution of Pore Radius 1-2 nm", Journal of Colloid and Interface Science, 1997, vol. 186, pp. 360-368.

Sing, "The use of nitrogen adsorption for the characterisation of porous materials", Colloids and Surfaces, A: Physicochemical and Engineering Aspects 187-188, 2001, pp. 3-9.

International Search Report for PCT International Application No. PCT/US2013/074100, mailed on Jun. 2, 2014, 4pgs.

* cited by examiner

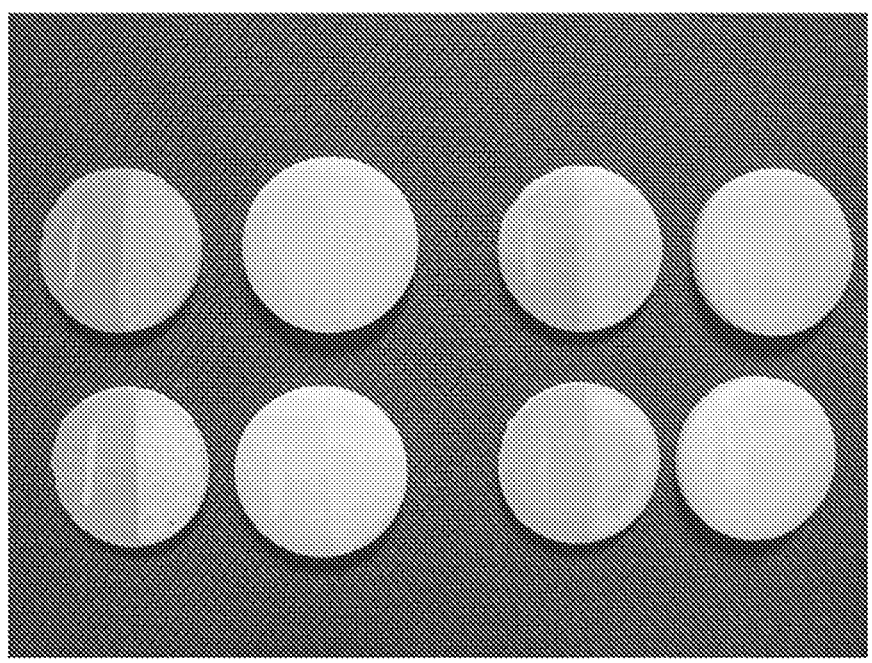

WHITENING COMPOSITION FOR TREATING THE SURFACE OF DENTAL CERAMIC AND RELATED METHODS

FIELD OF THE INVENTION

The invention relates to a process of treating parts of the surface of a porous dental zirconia article. The invention also relates to a composition which can be used in such a process, wherein the composition comprises a liquid and a whitening agent.

BACKGROUND OF THE INVENTION

A dental ceramic can be colored e.g. by incorporating pigments into the ceramic material from the very beginning or using metal salts containing solutions which are applied on the surface of a porous dental ceramic article with the aim to color the dental ceramic article in its entirety. Coloring solutions are described in a couple of documents: WO 2004/110959 relates to a coloring solution for ceramic framework. The solution comprises a solvent (e.g. water), a metal salt and polyethylene glycol having a Mn in the range of 1.000 to 200.000.

WO 00/46168 A1 (corresponding to U.S. Pat. No. 6,709, 694 B1) refers to coloring ceramics by way of ionic or complex-containing solutions containing defined concentrations of at least one salts or complexes of the rare earth elements or of the elements of the subgroups. The solution might contain additives like stabilizers, complex builders, pigments and beating additives.

WO 2008/098157 relates to a coloring solution for dental ceramic framework comprising a solvent, a coloring agent comprising metal ions, and a complexing agent, wherein the amount of complexing agent is sufficient to dissolve the coloring agent in the solvent.

WO 2009/014903 relates to a coloring solution for dental ceramic articles, the solution comprising a solvent and a coloring agent comprising rare earth element ions being present in the solution in an amount of at least about 0.05 mol/l solvent and transition ions being present in the solution in an amount of about 0.00001 to about 0.05 mol/l solvent.

In U.S. Patent Application Ser. No. 61/545,243 (3M IPC) aerogels, calcined and crystalline articles and methods of making the same are described. The content of this application is herewith incorporated by reference.

Sometimes, however, it is also desirable to use a whitening agent. Whitening agents are typically used to cover the metallic surface of a metallic dental framework in order to give the final dental restoration a more natural appearance. In certain cases, it can also be desirable to opacify e.g. the inner surface of a ceramic framework to cover discolorations of the tooth stump.

Compositions for whitening or opacifying dental metallic restorations are available in the market. Those compositions typically form a separate layer on the surface of the metallic framework and do not become part of the framework. These compositions often contain alumina as a whitening pigment to achieve the desired whitening effect. However, there is still room for improvement especially with regard to the requirements to be fulfilled with respect to modern dental materials. The present invention is intended to improve the known coloring and/or whitening processes.

SUMMARY OF THE INVENTION

In particular, it would be desirable to have a composition, which can be used to individualize especially parts of the outer surface of a porous dental ceramic and/or to treat the inner surface of a porous dental ceramic.

Moreover, it would be desirable if this can be done without a complete diffusion of the composition into the pores of pre-sintered or porous dental ceramic so that a defined application of the composition can be accomplished, if desired.

At least one of these objects can be achieve by providing a process of treating only parts of the surface of a porous dental zirconia article comprising the steps of:
 a) providing a composition and a porous dental zirconia article having an outer and inner surface,
 b) applying the composition preferably to only parts of the outer and/or inner surface of the porous dental zirconia article,
 c) optionally drying the porous dental zirconia article, and
 d) optionally firing the porous dental zirconia article,
the composition comprising:
 a liquid being miscible with water, but not being water,
 a whitening agent comprising nano-sized metal oxide particles, metal ion containing components or mixtures thereof,
 a stabilizer being selected from acid, base, complexing agent or mixture thereof,
the porous dental zirconia article showing a N2 adsorption and/or desorption of isotherm type IV according to IUPAC classification.

According to a further aspect the invention relates to a composition especially suitable for selective application to parts of the inner or outer surface of a porous dental zirconia article comprising:
 a liquid being miscible with water, but not being water,
 a whitening agent comprising nano-sized metal oxide particles, metal ion containing components or mixtures thereof,
 a stabilizer including acid, base, complexing agent or mixture thereof.

In another aspect, the invention relates to a dental zirconia article having been treated with the composition or obtainable by the process described in the present text. In a further aspect, the invention relates to the use of the composition as described in the present text for whitening parts of the outer and/or inner surface of a dental zirconia article.

In a further aspect the invention relates to a kit of parts comprising at least one receptacle containing the composition as described in the present text and a receptacle containing a coloring liquid as described in the present text, optionally application and mixing appliances and at least one porous dental zirconia article as described in the present text.

Unless defined differently, for this description the following terms shall have the given meaning:

A "liquid" is any substance which is able to solubilise, dissolve or disperse the whitening agent. The liquid should be sufficiently chemically stable if combined with the whitening agent. That is, the liquid shall not be decomposed by the other components present in the composition.

"Soluble" means that a component (solid) can be completely dissolved within a solvent.

That is, the substance is able to form individual molecules (like glucose) or ions (like sodium chloride) or non-settling particles (like a sol) when dispersed in water at 23° C. The solution process, however, might take some time, e.g. stirring the composition over a couple of hours (e.g. 10 or 20 h) might be required.

More specifically, according to the invention a substance or composition is defined as "soluble", if less than about 10 wt.-% or less than about 5 wt.-% or less than about 2 wt.-% or less than about 1 wt-% or less than about 0.1 wt.-% (with respect to the whole composition) of solid substance remains after the following procedure:

a. 800 mg of substance and 8.0 g of solvent are placed into a centrifuge test tube of known weight.

b. The test tube is closed and shaken for 60 minutes.

c. The mixture is centrifuged with centrifugal acceleration (ac) of 9870 m/s$^2$ for 20 min.

d. The supernatant liquid is decanted.

e. The precipitate is re-suspended with 6 g solvent.

f. The test tube is shaken for 60 min, centrifuged as described above, and the supernatant liquid decanted again.

g. Steps e) and f) are repeated one time.

h. The remaining precipitate is calcined for 12 h at 500° C. (+/−3.5° C.).

i. After cooling to room temperature the dry weight of the sample is determined and used for calculating the soluble fraction.

A substance or composition is defined as "insoluble", if more than about 90 wt.-% or more than about 50 wt.-% or more than about 25 wt.-% or more than about 10 wt.-% (with respect to the whole composition) of substance remains unsolved after the procedure described above.

The term "water-miscible" or "miscible with water" means that a certain liquid is miscible with water at 23° C. at least to a high extend to provide a homogeneous solution, i.e. without phase separation. More specifically, the water-miscible liquid is defined as miscible with water if at least 10 g or at least 100 g or at least 500 g or at least 750 g or least 1000 g water-miscible liquid is soluble in 1000 g water without phase separation. Ideally, no phase separation occurs at ambient conditions independent from the mixing ratio (e.g. ethanol is miscible with water in all ratios).

The term "amount sufficient to dissolve" describes the amount of an agent needed to fully dissolve a certain substance in a certain solvent so that a storage stable composition can be obtained. The time needed to dissolve a substance is not particularly limited, however, the dissolution should occur within a reasonable time (e.g. within about 10 to about 48 h) using common equipment like mechanical stirrers and heaters.

A solution can be classified as "storage stable", if it remains stable over a considerable long period of time (at least about 4 weeks to more than about 12 months under ambient conditions). A storage stable solution typically does not show any visible (visible to the human eye) precipitation of the coloring agent during storage at ambient conditions (about 23° C., about 1013 mbar) and does not show decomposition of the solution or precipitation of single or multiple components.

"Non-water based" means that the major part (at least more than about 50 or more than about 60 or more than about 70 or more than about 80 or more than about 90 wt.-%) of the liquid components being present in the composition or solution is/are components being different from water.

A "whitening agent" is an agent, which is able to whiten the surface of a dental ceramic either right after treatment of the ceramic with the whitening agent or after conducting a firing step of the treated ceramic. The whitening effect typically goes along with an increase in opacity.

"Agglomeration" means the formation of a mass being comprised of particles. An example for an agglomeration is the formation of a precipitate of a chemical substance, which might be caused by the formation salt being insoluble or hardly soluble in a liquid or solvent. Another example for an agglomeration is the formation of aggregates from e.g. previously nano-sized particles, which might be caused by a disturbance of the stabilizing solvent environment. Exemplifying evidence for an agglomeration is the precipitation of a solid from a solution or liquid, or the clouding of the solution or liquid e.g. caused by a change of the pH value.

A "complexing agent" is any agent which is able to form complexes with the whitening agent. A "complex", also known as coordination compound, in chemistry usually is used to describe molecules or ensembles formed by the combination of ligands and metal ions. Originally, a complex implied a reversible association of molecules, atoms, or ions through weak chemical bonds. As applied to coordination chemistry, this meaning has evolved. Some metal complexes are formed virtually irreversibly and many are bound together by bonds that are quite strong. The ions or molecules surrounding the metal are called ligands. Ligands are generally bound to a metal ion by a coordinative bonding (donating electrons from a lone electron pair to the Lewis acidic metal center), and are thus said to be coordinated to the ion. Those ligands are referred to as "coordinating ligands".

Rare earth elements and/or of the subgroups of the rare earth elements include Ce, Pr, Nd, Sm, Eu, Gd, Tb, Dy, Ho, Er, Tm, Yb and Lu. Transition metals comprise the metals listed in the columns of the Periodic Table of Elements starting with the elements Sc, Ti, V, Cr, Mn, Fe, Co, Ni, Cu and Zn and the metals listed below those elements.

Metals of the main groups comprise the metals listed in the main groups of the Periodic Table of Elements starting with the elements Li, Be, B, C, N, O, F and the metals listed below those elements.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

"Filler" means particles dispersed in curable organic substances or monomers to adjust physical properties like hardness or flexural strength. The whitening agent described in the present text is not regarded as a filler.

The term "dental article" means any article which can or is to be used in the dental field, especially for producing of or as dental restoration, a tooth model and parts thereof. In this respect, a dental ceramic article has typically a certain shape. A dental ceramic article has usually a 3-dimensional inner and outer surface including convex and concave structures. Compared to other ceramic articles such as pottery or paving stones, the dental ceramic article is small and filigree. The thickness of the dental ceramic article can vary from very thin, e.g. at the edges and rims (below about 0.1 mm) to considerably thick, e.g. in the biting area (up to about 7 mm) Typically, the dental ceramic article described in the present text comprises or essentially consists of a polycrystalline ceramic material comprising yttrium stabilized zirconia.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons) and parts thereof. The surface of a tooth is considered not to be a dental article.

A dental article should not contain components which are detrimental to the patient's health and thus free of hazardous and toxic components being able to migrate out of the dental article.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

A dental ceramic article is classified as "pre-sintered" if the dental ceramic article has been treated with heat (temperature range from about 900 to about 1100° C.) for about 1 to about 3 h to such an extent that the raw breaking resistance of the dental ceramic measured according to the "punch on three ball test" ISO 6872 is within a range of about 15 to about 55 MPa or about 30 to about 50 MPa. A pre-sintered dental ceramic article usually has a porous structure and its density (usually 3.0 g/cm³ for an Yttrium stabilized $ZrO_2$ ceramic) is less compared to a completely sintered dental ceramic framework (usually 6.1 g/cm³ for an Yttrium stabilized $ZrO_2$ ceramic). A dental ceramic article is classified as "absorbent" if the dental ceramic article is able to absorb a certain amount of a liquid composition, comparable to a sponge. The amount of composition which can be absorbed depends e.g. on the chemical nature of the dental ceramic article, the viscosity of the composition, the porosity and pore volume of the dental ceramic article.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between about 15% and about 75% or between about 18% and about 75%, or between about 30% and about 70%, or between about 34% and about 67%, or between about 40% to about 68%, or between about 42% and about 67%.

The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

A dental ceramic article can be characterized as "homogeneously colored", if no color spots can be identified with the human eye on the surface of the dental ceramic article after the sintering process. More precisely, this can be proven e.g. using a commercially available Hunter Lab System or the system GretagMacbeth Color i7. If desired, the homogeneity can be measured according to DIN 5033 Measurement of Colors; Parts 1-8 (Normvalenz-System, L*a*b*-Farbraum nach CIE, 1976); DIN 6174 Farbmetrische Bestimmung von Farbabständen bei Körperfarben nach der CIE-LAB-Formel; DIN 55981 (ISO 787-25) Farbabstandsbestimmung ΔE* using standard operating procedures according to the manufacturer's operation manual (Hunter Lab., Corp.) to determine the sample dimension, the calibration and measure procedure. Further hints to this measuring system can also be found in DE 100 52 203 A1 on page 3, line 56 to page 4, line 6 (corresponding to U.S. Pat. No. 6,756,421, column 4, lines 26 to 55).

"Zirconia ceramic article" shall mean a 3-dimensional article wherein at least one the x, y, z dimension is at least about 5 mm, the article being comprised of at least about 80 wt.-% or at least about 90 wt.-% zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monocline, cubic zirconia and mixtures thereof.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former.

The porous ceramic dental material described in the present text does not contain a glass. "Glass-ceramic" means an inorganic non-metallic material where one or more crystalline phases are surrounded by a glassy phase so that the material comprises a glass material and a ceramic material in a combination or mixture. It is formed as a glass, and then made to crystallize partly by heat treatment. Glass ceramics may refer to a mixture of lithium-, silicon-, and aluminium-oxides.

The porous dental material described in the present text does not contain a glass-ceramic. "Sol" refers to a continuous liquid phase containing discrete particles having sizes in a range from 1 nm to 100 nm.

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

The term "aerogel" shall mean a three-dimensional low density (i.e., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than about +/−5% or +/−2% or +/−1%.

The term "tubular reactor" refers to the portion of a continuous hydrothermal reactor system that is heated (i.e., the heated zone). The tubular reactor can be in any suitable shape. The shape of the tubular reactor is often selected based on the desired length of the tubular reactor and the method used to heat the tubular reactor. For example, the tubular reactor can be straight, U-shaped, or coiled. The interior potion of the tubular reactor can be empty or can contain baffles, balls, or other known mixing techniques.

"Casting" means a manufacturing process by which a liquid material (e.g. solution or dispersion) is poured into a mould, which contains a hollow cavity of the desired shape, and then allowed to solidify.

"Density" means the ratio of mass to volume of an object. The unit of density is typically g/cm³. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

The term "calcining" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase). Sintering of firing means making objects from a compressed powder by heating the material (typically below its melting point—solid state sintering) until its particles adhere to each other.

By "machining" is meant milling, grinding, drilling, cutting, carving, or substractive shaping a material by a machine. Milling is usually faster and more cost effective than grinding. A "machinable article" is an article having a 3-dimensional shape and having sufficient strength to be machined.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1025 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.). The term "comprising" includes also the more limited expressions "consisting essentially of" and "consisting of".

BRIEF DESCRIPTION OF THE FIGURES

FIG. 1 shows sintered zirconia discs to which opacifying compositions described in the present text have been applied.

DETAILED DESCRIPTION

In the dental field, water-based coloring liquids are commonly used for coloring especially zirconia based dental ceramic frameworks in a pre-sintered or porous stage. This is typically achieved by dipping the framework into a coloring solution in its entirety. By doing so, a homogenous color of the whole dental ceramic is usually achieved.

However, if individual coloration or whitening in small defined areas is desired, the water-based liquids of the prior art cannot be used because the different colors typically will mix up and diffuse into parts of the ceramic article where they are not supposed to be present.

The inventive solution or composition solves this problem by allowing a dental technician to selectively apply a whitening agent to parts of the surface of a dental ceramic e.g. using a brush. It was found that the whitening agent remains on the spot or area of the surface where the composition has been applied to and does typically not diffuse through the rest of the material of the porous dental ceramic.

Thus, the invention enables the local and specific application of a whitening agent to selective parts of the surface of a ceramic material. It allows an exact whitening of individual parts of the surface of a dental ceramic. This may facilitate the imitation of white spots, which can sometimes be found on natural teeth.

If desired, the composition can also be used to apply an opaque surface layer to the inner and/or outer surface of a translucent dental ceramic, especially dental ceramic frameworks or dental monolithic ceramic restorations. In this respect, especially Al and Ti components containing whitening agents were found to be useful.

The composition is typically applied to the surface of pre-sintered, porous dental ceramic. The painted features remain essentially sharp even if the bulk of the dental ceramic is still wet from a prior coloring step.

Thus, the composition can also be applied to the surface of wetted dental ceramics, which have already been colored by using a commercially available water-based coloring liquid, without the risk of the color spreading indiscriminately due to diffusion.

On the other hand the composition is also compatible with water-based coloring liquids in the sense that application of the composition will not affect the subjacent "background color" of the dental ceramic having already been treated with a water-based coloring liquid in an undesired manner.

If desired, the whitening impression produced by the composition in the material can be further adjusted by diluting the composition with a dilution liquid or simply with more solvent. Without wishing to be bound to a particular theory, a possible explanation for this finding is as follows:

If the composition is applied to a dry, porous material, it will migrate into the pores of the material. But this happens only to a very limited extent, mainly due to the comparably high viscosity of the composition. If the composition, however, is applied to a water-soaked, porous material, the water-soluble solvent will mix with the water already present inside the pores of the ceramic material. The whitening agent, however, especially when present in the form of particles will not be able to diffuse through the pore system freely and remains in the area to which it has been applied.

Thus, by mixing a (e.g. water-soluble or water-dispersible) whitening agent, a stabilizer and a water-soluble liquid, which is able to take up, solve or stabilize the whitening agent in the liquid one or more of the above mentioned objective(s) (e.g. sufficiently high viscosity) can be achieved.

Moreover, it was found that the inventive composition(s) remain stable over a considerable long period of time. They typically do not show visible (to the human eye) precipitation of the whitening agent during storage at ambient conditions (23° C., normal pressure).

Other embodiments, features and advantages of the present invention will be apparent from the following detailed description, drawings, and claims.

The composition is used for being selectively applied to parts of the surface of a dental ceramic article. That is, the composition is only applied to parts of the surface of the dental ceramic article but not to the whole (inner and outer) surface. In contrast to commercially available coloring liquids, the dental ceramic article is not dipped completely into the composition described in the present text Moreover, the composition cannot only be applied to dry surfaces of dental ceramic articles, but also to the surface of wetted dental ceramic articles, especially to the surface of pre-sintered or porous dental ceramic articles.

The composition typically has an adequate viscosity so that a sufficient amount of composition can be applied to the surface of the dental ceramic article.

According to one embodiment, the composition has a viscosity above about 10 or above about 50 or above about 100 mPa*s (measured at 23° C. with a shear rate of 50 $s^{-1}$). The viscosity of the composition is typically below about 10,000 or below about 5,000 or below about 2,000 mPa*s (measured at 23° C. with a shear rate of 50 $s^{-1}$).

Typical viscosity ranges include from about 10 to about 10,000 or from about 20 to about 8,000 or from about 50 to about 5,000 mPa*s (measured at 23° C. with a shear rate of 50 $s^{-1}$). If the viscosity of the composition is too high, the whitening agent might not be able to enter the pores of the ceramic material at all. On the other hand, if the viscosity of the composition is too low, the whitening agent might diffuse through the pores too much.

If desired, the measurement of the viscosity can be done as follows: A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to 50 $s^{-1}$. The measurement is done 500 s after starting the shearing process of the composition.

Thus, the composition is typically in the form of a liquid which can be applied onto the surface of either a dry or wet, optionally pre-colored, porous zirconia based dental ceramic article. If the porous zirconia is already wetted, the composition will solve into the geometry within minutes and disappear from the surface.

If the composition is used in excess, not all of it will migrate into the pores of the porous zirconia based material. The composition remaining on the surface can be wiped off, if desired, before or after sintering without problems.

Measurement of the pH-value can be achieved by means known by the person skilled in art. E.g. an instrument like Metrohm™ 826 or pH indicator paper can be used.

For water-free compositions, the pH-value can be determined as follows: The composition may be mixed with a certain amount of water (e.g. 1:1) and the pH value measured in the above stated manner. In one embodiment the composition is transparent.

A composition can be characterized as transparent within the meaning of the invention if a beam of visible light (about 400 to about 700 nm) is not scattered by the solution and the solution does not appear to be turbid. Providing a transparent composition can be desirable in that the whitening agent being contained in the composition is either a real solution (e.g. dissociation into ions) or a dispersion (e.g. particle size smaller than wavelength of visible light).

The composition comprises a whitening agent which comprises components which may agglomerate and/or precipitate if the composition is adjusted to a certain pH value.

If desired, agglomeration and/or precipitation of the components can be initiated by simply changing the pH value of the solution, e.g. by drop-wise adding an acid or base like HCl or NaOH (e.g. 1 molar solution) to the composition and measuring the pH value.

If the composition was initially transparent, white clouds will appear in the composition indicating that the components started to agglomerate. The agglomeration can continue and finally result in a precipitation of the agglomerated components over time (e.g. after about 1 h). As outlined above, the agglomeration might be caused by the formation of components being insoluble or hardly soluble within the liquid used.

The agglomeration and/or precipitation might also be caused by destabilizing the outer shell of solvent molecules surrounding and stabilizing e.g. nano-sized particles.

The components being contained in the whitening agent may include metal cations, nano-sized particles of metal oxides and mixtures thereof. Examples of components used for or contained in the whitening agents include cations and oxides of Ti, Al, Zr and mixtures thereof. By choosing these kinds of components, the crystal structure of the dental ceramic and thus its mechanical strength is typically not negatively affected during sintering. In contrast to this, choosing a different kind of component may lead to a disruption of the crystal structure, inclusions, etc. during sintering, thus severely hampering the material's mechanical strength. E.g. using silicon or silica containing whitening agent for zirconia based dental ceramic articles, may lead to a decrease in strength of the sintered dental ceramic by up to about 80%. Similarly, using zirconium or zirconia might cause density inhomogeneities and/or distorsions in the material, which is typically not desired.

According to one embodiment, the whitening agent is water-soluble. The whitening agent can comprise, essentially consist of or consist of a salt comprising metal cations and anions, wherein the anions are selected from the group consisting of $OH^-$, $NO_3^-$, $NO_2^-$, $CO_3^{2-}$, $HCO_3^-$, ONC, halogen anions (fluoride, chloride, bromide), acetates, alkoxides and mixtures thereof. As described in more detail below, a complexing agent can be added as a separate component. However, it is also feasible that the complexing agent is at least partially identical with the anion of the whitening agent, or that the anion of the whitening agent can be classified as complexing agent as well.

Examples for these kinds of anions include gluturate, lactate, gluconate, propionate, butyrate, glucuronate, benzoate, phenolate, citrate, salicylate, glycinate, acetylacetonate, propylendiamine, ascorbate and others.

Besides or in addition to metal cations, the whitening agent comprises nano-sized particles. Thus, the whitening agent comprises metal cations or nano-sized particles or a mixture of both (metal cations and nano-sized particles), wherein the presence of nano-sized particles can sometimes be preferred.

Nano-sized particles typically have a (hydrodynamic) diameter in the range from about 1 nm to about 500 nm or from about 2 nm to about 100 nm or from about 3 nm to about 20 nm. The diameter should be tailored to be compatible with (i.e. being smaller than) the pore size of the ceramic material to which the composition should be applied.

If desired, the (hydrodynamic) diameter of the particles can be determined by a dynamic light scattering method. Dynamic Light Scattering (DLS) is an analytical method using the Brownian motion of particles in a solvent to determine their size. Basis of the method is that smaller particles move faster than bigger particles. A laser is used to irradiate a sample and the light scattered by the particles is detected. Small, fast moving particles cause quick fluctuations of the detected signal, while bigger and slower particles cause slower fluctuations.

The DLS method determines the so called "hydrodynamic diameter" of the dispersed particles. The moving particles possess a shell of solvent that moves along with them through the solution. The hydrodynamic diameter is the diameter of the solid particle plus the solvent shell. As a result, the actual particle is always smaller than the measured diameter.

A device which can be used for the DLS measurements is the Zetasizer™ Nano ZS (Malvern). The nano-sized particles may comprise, essentially consist of or consist of $ZrO_2$, $Al_2O_3$ or $TiO_2$ particles, wherein $TiO_2$ and $Al_2O_3$ based components are sometimes preferred. According to one embodiment, the nano-sized particles may comprise, essentially consist of or consist of $Al_2O_3$.

Within this invention, nano-sized particles are not regarded as filler or filler particles. Filler or filler particles typically precipitate from a liquid composition during storage. Thus, in contrast to nano-sized particles, fillers can typically be separated by filtration.

The amount of whitening agent used is not particularly limited unless the result to be achieved cannot be obtained. The metal ions are contained in the solution in an amount sufficient to achieve an adequate effect within the dental ceramic.

Good results can be achieved e.g. with amounts (calculated with respect to the metal) in the range of about 1 to about 20% by weight of whitening agent or in the range of about 3 to about 15% by weight, or in the range of about 4 to about 12% by weight with respect to the weight of the whole composition.

If the amount of whitening agent used is too low, the effects obtained in the ceramic might be too weak for the intended use.

If the amount of whitening agent used is too high, it can be difficult to produce a solution. So, there might remain large particles within the composition, which can cause undesired shading effects on the surface of the dental ceramic or influence other material properties.

The composition comprises a liquid. The liquid is miscible with water. The liquid, however, is not water. Typically, the liquid can be characterized by at least one of the following features:
  molecular weight (Mw): from about 30 to about 1,000 g/mol or from about 60 to about 400 g/mol;
  viscosity: from about 1 to about 2,000 mPa*s or from about 100 to about 1,500 mPa*s or from about 200 to about 1,000 mPa*s (measured at 23° C. at a shear rate of 50 s$^{-1}$);
  free of polymerizable groups like (meth)acrylate groups, epoxy groups, carbon-carbon unsaturated groups;
  not containing elements like S, P.

Mw (substance) is the average molecular weight of the respective substance used. Liquids which can be used include polyalcohols including ethylene glycol, polyethylene glycols, glycerol and mixtures thereof.

Polyethylene glycols which can be used can be represented by formula (1)

R1O—(CH2-CH2-O)m-R1     (1)

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and
m=about 2 to about 100, preferably about 2 to about 20, more preferably about 2 to about 5

The average molecular weight (Mw) of the polyethylene glycol should be in the range of about 100 to about 5.000, preferably in the range of about 100 to about 1.000, more preferably in the range of about 100 to about 400.

If desired, the average molecular weight (Mw) can be determined according to procedures known to a person skilled in the art as described for example in Arndt/Müller, Polymercharakterisierung, Hanse Verlag, 1996. Depending on the molecular weight to be determined, it might be necessary to apply different measurement methods (see below).

Most PEGs (polyethylene glycols) include molecules with a distribution of molecular weights, i.e. they are polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy.

Specific examples of water-miscible liquid, which can be used, include polyol(s) (including polyvinyl alcohol), glycol ether(s) (e.g, PEG 200, PEG 400, PEG 600, diethylene glycol methyl ether, diethylene glycol ethyl ether), alcohol(s) (including 1,2-propanediol, 1,3-propanediol, ethanol, (n- and iso-)propanol, glycerol), glycerol ether, and mixtures thereof. In particular, the following liquids were found to be useful: glycerol, ethylene glycol, propylene glycol and mixtures thereof.

According to one embodiment, the liquid should be able to dissolve the whitening agent. Dissolving means that the composition does not contain particles being visible to the human eye. The amount of liquid used is not particularly limited unless the result to be achieved cannot be obtained. The liquid is typically used in an amount of at least about 20 or at least about 50 or at least about 70 wt.-% with respect to the whole weight of the solution.

There is no particular upper amount, however, the liquid is typically used up to an amount of up to about 98 or up to about 96 or up to about 90 wt.-% with respect to the whole weight of the composition. Useful ranges for the liquid include from about 20 to about 98 wt.-% or from about 50 to about 96 wt.-% or from about 70 to about 90 wt.-% with respect to the whole weight of the composition.

Besides or in addition to a complexing agent, the composition may contain an acid or base. Complexing agent(s), acid(s) and base(s) are embodiments for stabilizers. The stabilizers help to prevent or reduce agglomeration or precipitation of the whitening agent in the composition. The whitening agent thus usually remains in a dispersed stage without settling.

The acid or base used may contain water or is essentially water-free but should be solvable in the liquid used. Examples of acids which can be used include organic acids (like acetic acid, citric acid, malonic acid), inorganic acids (e.g. hydrochloric acid, nitric acid, sulfuric acid) and mixtures thereof, wherein the use of organic acids is sometimes preferred.

The acid is typically used in an amount sufficient to adjust the pH value of the composition to below about 5 or below about 4.5 or below about 4 or below about 3.5 or below about 3. Examples of bases which can be used include ammonia, amines and mixtures thereof, wherein the use of ammonia is sometimes preferred.

The base is typically used in an amount sufficient to adjust the pH value of the composition to above about 9 or above about 9.5 or above about 10 or above about 10.5 or above about 11. The acid or base is typically present in an amount of at least about 1 or at least about 5 or at least about 10 wt.-% with respect to the weight of the composition. The acid or base is typically present in an amount of at most about 75 or at most about 50 or at most about 20 wt.-% with respect to the weight of the composition.

Typical ranges for the acid or base include from about 1 to about 75 or from about 5 to about 50 or from about 10 to about 20 wt.-% with respect to the weight of the composition. If the amount of acid or base used is outside the above mentioned ranges, the components of the whitening agent might already start to agglomerate and to precipitate prior to use. This might negatively affect the storage stability.

According to one embodiment the composition contains water. Water can be present in an amount from about 1 to about 60 wt.-% or from about 2 to about 50 wt.-% or from about 5 to about 20 wt.-% with respect to the weight of the whole composition. According to another embodiment the composition is a non-water based composition. Essentially free of water means that the composition does not contain water, which has been willfully added as a solvent. However, traces of water being present in the composition due to the components used are acceptable. Thus, this term includes that water might be present up to an amount of about 10 wt.-% or up to about 7 wt.-% or up to about 5 wt.-% or up to about 2 wt.-% or up to about 1 wt.-% with respect to the whole solution or composition, respectively.

Providing a non-water based composition can be beneficial in that the migration of the composition into the pores of the porous dental ceramic is further reduced. This can be especially useful, if the dental ceramic has already been treated with a water-based substance, e.g. a coloring solution. Another advantage is that the composition cannot dry out (given that the liquid used is high boiling), which is a major advantage regarding handling of the composition.

Besides or in addition to an acid or base, the composition may comprise a complexing agent. The complexing agent is able to form a complex with the metal ions of the whitening agent. The complex formed is typically soluble in the liquid. The complex formed may be better soluble in the liquid than in water.

Typically, if present, the complexing agent is present in the composition in an amount sufficient to dissolve the whitening agent in the liquid or to prevent precipitation of the whitening agent. The complexing agent can be present in an amount of at least about 1 wt.-% or at least about 5 wt.-% or at least about 10 wt.-% with respect to the amount of the whole composition. There is no upper limit, however, usually the amount of complexing agent used does not exceed an amount of about 50 wt.-% or about 40 wt.-% or about 30 wt.-% with respect to the amount of the whole composition.

E.g., the complexing agent can be used in an at least stoichiometric ratio with respect to the molar amount of the ions contained in the whitening agent. Good results can be achieved, if the ratio of molar amount of complexing agent to the molar amount of metal ion being present in the whitening agent is equal to or greater than about 1 or about 2 or about 3.

If the amount of complexing agent used is too low, the whitening agent might not be dissolved entirely. If the amount of complexing agent used is too high, the excess complexing agent itself might remain unsolved. The complexing agent is usually added as a separate component of the composition. However, it can also be added as part of the whitening agent, e.g. as counter ion to the metal ion being present in the whitening agent. Examples include citrate, acetate and acetylacetonate.

Without wishing to be bound by any theory, it is assumed that the complexing agent is able to form a complex with the metal ion(s) of the whitening agent assisting the agent in dissolving in the chosen solvent and preventing the whitening agent from precipitating from the composition especially during storage.

The increased stability of a chelated complex is called the chelate effect. In this respect, the complexing agent can also be characterized as a chelating agent (or a polydentate ligand), which can bond to more than one coordination site on the central atom. Because it is necessary to break all of the bonds to the central atom for the ligand to be completely displaced, it requires more energy to increase the number of separate molecules. If a chelate were replaced by several monodentate ligands (such as water or ammonia), the total number of molecules would decrease, whereas if several monodentate ligands were replaced by a chelate, the number of free molecules increases. The effect is therefore entropic in that more sites are used by less ligands and this leaves more unbonded molecules: a total increase in the number of molecules in solution and a corresponding increase in entropy.

According to the present invention the complexing agents can be classified as follows:
  Complexing agents with 6 coordinating ligands include EDTA (ethylene diamine tetra acetic acid); 18-crown-6; 2,2,2-crypatand; polymeric ligands like poly acrylate, poly asparagate, acidic peptides with an "infinite" number of coordinating ligands are counted as complexing agents with 6 coordinating ligands.
  Complexing agents with 5 coordinating ligands include 15-crown-5; cyclo-pentadien.
  Complexing agents with 4 coordinating ligands include NTA (nitrilotriacetate); 12-crown-4; triethylentetramine; porphin$^{2-}$; phthalocyanin$^2$ bis(salicilate)ethylenbis(imin)salen$^{2-}$.
  Complexing agents with 3 coordinating ligands include $C_3H_5O(COO)_3^{3-}$.
  Complexing agents with 2 coordinating ligands include $HC_6H_5O_7^{2-}$; salicylate, glycinate; lactate; acetylacetonate; propylendiamine; ascorbate $C_6H_6O_6^{2-}$; $C_3H_5O(COOH)(COO)_2^{2}$.

A citrate is an ionic form of citric acid, such as $C_3H_5O(COO)_3^{3-}$, that is, citric acid minus three hydrogen ions. Citrates are compounds containing this group, either ionic compounds, the salts, or analogous covalent compounds, esters. Since citric acid is a tribasic acid, intermediate ions exist, hydrogen citrate ion, $HC_6H_5O_7^{2-}$ and dihydrogen citrate ion, $H_2C_6H_5O_7^-$. These may form salts as well, called acid salts. Salts of the hydrogen citrate ions are weakly acidic, while salts of the citrate ion itself (with an inert cation such as sodium ion) are weakly basic.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions.

The inventive solution may also contain one or more additive(s). Additives which can be added to the composition include anti oxidant agents (e.g. components which contribute to stabilizing the solution against oxidation), such as methoxy phenol hydrochinone, Topanol A and mixtures thereof), buffers (such as acetate or amino buffers and mixtures thereof), preservative agents (such as sorbic acid or benzoic acid and mixtures thereof), soluble colorants (e.g. colorants which can be added to food) and mixtures thereof.

Adding soluble colorants can be beneficial in order to enhance the visibility of the composition during use, especially, if the composition is transparent. Thus, the practitioner can easily determine to which parts of the surface of the dental ceramic the composition has already been applied and which parts have not been treated yet and should remain untreated. On the other hand the soluble colorants which are typically of organic nature will be burnt during a later sintering step and thus not be incorporated into the crystal structure of the dental ceramic. Examples of soluble colorants which can be used include Riboflavin (E101), Ponceau 4R (E124), Green S (E142). There is no need for additive(s) to be present, however, if they are present, they are typically present in an amount which is not detrimental to the purpose to be achieved when applying the composition. If additive(s) are present, they are typically present in an amount of about 0.01 to about 10 wt.-% or from about 0.05 to about 5 wt.-% or from about 0.1 to about 3 wt.-% with respect to the whole composition.

The composition may comprise the components in the following amount:
- the liquid in an amount of about 20 to about 98 wt.-% or from about 70 to about 95 wt.-%,
- the whitening agent in an amount of about 1.0 to about 20 wt.-% or from about 3.0 to about 15 wt.-% (calculated with respect to the amount of metal contained therein),
- the stabilizer (including acid, base and/or complexing agent) in an amount of about 1 to about 75 wt.-% or from about 5 to about 50 wt.-%
- optionally additives in an amount of about 0 to about 10 wt.-% or from about 0.05 to about 5 wt.-%, wt.-% with respect to the whole composition.

The composition can be produced by a process comprising a mixing step. Mixing can be done at room temperature or by applying heat and/or while stirring. The pH value can be adjusted as needed.

Applying heat and/or stirring can be beneficial in order to accelerate the dissolution process of the whitening agent into the solvent. The composition is typically stirred until the whitening agent and the stabilizer are completely dissolved or dispersed in the liquid (e.g. from about 5 min to about 24 h). During this step, the formation of nano-sized particles can take place. Undesired precipitations can be removed by filtering, if desired. If desired, additives (like those mentioned above) can be added.

The dental ceramic article to which the composition is to be applied is porous and thus absorbent. Moreover, the dental ceramic article typically has an outer and an inner surface. The outer surface typically has an overall convex shape, whereas the inner surface typically has an overall concave shape.

The dental ceramic article onto which the solution is applied can be dry or wet. "Wet" means that the ceramic material still contains a small amount of water. However, there should be no visible spots of water residues on the surface.

A pre-sintered or porous material sample is considered wet, if the material has been completely dipped into water for about 10 s, removed from the water and wrapped for about 10 s into a paper tissue being able to absorb water or alternatively, if a water-based solution has been applied to large areas of the material using e.g. a sponge, a brush, etc.

The surface of a pre-sintered or porous material sample is considered dry, if the material has been completely dipped into a water-based solution for about 10 s, removed from the water, wrapped for about 10 s into a paper tissue being able to absorb water and placed into an oven for about 1 h at a temperature of about 200° C. or left to dry open to the air for about 4 h, or if no water-based solution has been applied to the pre-sintered or porous ceramic at all. If desired, the dental ceramic article can be pre-colored using coloring solutions which are already known in the art.

If the coloring solution, which provides a background color to the dental ceramic article, possesses a pH value at which the composition is not stable, the coloring solution will facilitate precipitation of the whitening agent being contained in the composition shortly after entering the porous material and fix it to the intended position.

The composition described in the present text is applied to the surface of a porous dental ceramic article comprising or preferably consisting essentially of zirconia.

The term "consisting essentially of" means that the major part (e.g. greater than about 80 or about 85 or about 90 wt.-%) of the dental ceramic is based on $ZrO_2$. The rest may be comprised of oxides selected from $HfO_2$ and stabilizers including $Y_2O_3$, CaO, MgO, $CeO_2$ or mixtures thereof.

Ceramic materials which can be used for providing a dental ceramic article or as dental ceramic article are described in U.S. application No. 61/545,243 filed Oct. 10, 2011. The ceramic materials described in that application are often highly translucent and are prepared by using a sol/gel process. Especially in combination with those highly translucent materials the inventive process and composition described in the present text can be beneficial. According to one embodiment, the porous dental ceramic article is a $ZrO_2$ based ceramic which is preferably stabilized with $Y_2O_3$. The dental ceramic is typically in a pre-sintered stage.

It was found that a material showing a N2 adsorption and/or desorption of isotherm type IV (according to IUPAC classification) and/or adsorption desorption isotherms with a hysteresis loop (especially in a $p/p_0$ range of 0.70 to 0.95) is particularly suitable to be treated with the whitening composition described in the present text.

Commercially available Y-TZP ceramic materials typically show a N2 adsorption and/or desorption of isotherm type II (according IUPAC classification), which was found to be less effective for producing an aesthetic dental article in an efficient way. Materials showing a type II isotherm are said to be macro-porous, whereas materials showing a type IV isotherm are said to be meso-porous.

Materials showing a type II isotherm adsorption and/or desorption behaviour tend to a more diffuse and less precise absorption of the whitening composition. This may have the effect that the whitening composition applied is not precisely visible on the surface of the dental article especially after having conducted a sintering step. In contrast to this, the porous dental zirconia article described in the present text has an absorption behaviour which is more beneficial, especially with respect to a whitening composition.

Analyzing the adsorption and/or desorption behaviour of ceramic materials for characterisation of pores is a process well known in the art (cf. e.g. Kenneth Sing; The use of nitrogen adsorption for the characterisation of porous materials; Colloids and Surfaces; A: Physicochemical and Engineering Aspects 187-188 (2001) 3-9).

The liquid contained in the whitening composition is typically absorbed very quickly having the effect that the diffusion of the whitening agent is essentially limited to those areas to which the whitening composition has been applied.

Using the porous dental zirconia article described in the present text has the further benefit that triggering the precipitation of the whitening agent from the composition by additional means e.g. adjusting the pH value is not needed. The stabilizer can therefore be chosen from a wide variety of components including acid(s), base(s) and complexing agent(s).

If desired, the dental ceramic article described in the present text can be further individualized manually, e.g. using a file, a cutter or carving tool, if desired. The material (before sintering) is sufficiently hard to allow a precise machining but not too hard or too strong to prevent manually individualization. In contrast to this, commercially available zirconia materials are often too soft and thus allow no precise carving or modelling in a pre-sintered stage.

Thus, using the porous dental ceramic article described in the present text will facilitate the production of high quality and aesthetic dental restoration(s) which can be easily individualized by treating parts of the surface with a whitening composition.

The zirconia material described in the present text shows a variety of well balanced features (e.g. sufficient strength to be machined, adequate strength to be manually individualized, reduced wear of machining tools and/or reduced production of dust during machining)

In contrast to zirconia material described in the art, the zirconia material described in the present text is more translucent after sintering. A whitening composition applied to this material will thus become better visible compared to whitening compositions applied to less translucent or more opaque zirconia material. The porous zirconia article shows a N2 adsorption and/or desorption of isotherm type IV according to IUPAC classification. Further, the porous zirconia article typically has a Vickers hardness from about 25 to about 150 or from about 35 (HV 0.5) to about 150 (HV 1).

According to one embodiment, the porous zirconia article described in the present text can be characterized by at least one of the following features:
  (a) showing a $N_2$ adsorption and/or desorption isotherm with a hysteresis loop;
  (b) showing a $N_2$ adsorption and desorption of isotherm type IV according to IUPAC classification and a hysteresis loop;
  (c) showing a $N_2$ adsorption and desorption isotherm of type IV with a hysteresis loop of type H1 according to IUPAC classification;
  (d) showing a $N_2$ adsorption and desorption isotherm of type IV with a hysteresis loop of type H1 according to IUPAC classification in a $p/p_0$ range of 0.70 to 0.95;
  (e) average connected pore diameter: from about 10 to about 100 nm or from about 10 to about 80 nm or from about 10 to about 70 nm or from about 10 to about 50 nm or from about 15 to about 40;
  (f) average grain size: less than about 100 nm or less than about 80 nm or less than about 60 nm or from about 10 to about 100 or from about 15 to about 60 nm;
  (g) BET surface: from about 10 to about 200 $m^2/g$ or from about 15 to about 100 $m^2/g$ or from about 16 to about 60 $m^2/g$;
  (h) biaxial flexural strength: from about 10 to about 40 or from about 15 to about 30 MPa;
  (i) Vickers hardness: from about 25 (HV 0.5) to about 150 or from about 35 to about 140 (HV 1).
  (j) x, y, z dimension: at least about 5 mm or at least about 10 or at least about 20 mm;

A combination of the following features was found to be particularly beneficial: (a) and (h), or (a) and (b) and (h), or (b) and (c), or (c), (e), (g) and (h).

If desired the above features can be determined as described in the Example section. It was found that material showing a $N_2$ adsorption and/or desorption of isotherm type IV (according to IUPAC classification) and/or adsorption desorption isotherms with a hysteresis loop (especially in a $p/p_0$ range of 0.70 to 0.95) are particularly suitable.

The BET surface of porous zirconia materials described in the prior art is typically within a range from 2 to 9 $m^2/g$, whereas the BET surface of the porous zirconia materials described in the present text is preferably above 10 $m^2/g$. The average grain size of the zirconia particles in the porous zirconia article described in the present text is small compared to the average grain size of the material of commercially available zirconia materials.

A small grain size can be beneficial in that it typically leads to a more homogeneous material (from a chemical perspective), which may also result in more homogeneous physical properties.

Useful ranges for the x, y and z dimensions include from about 5 to about 300 or from about 8 to about 200 mm. It was found that it is beneficial for certain properties, if the porous zirconia material has a certain average connected pore diameter. The average connected pore diameter should be in a particular range. It should not be too small and also not be too large.

The porous zirconia material described in the present text and used for providing the porous dental ceramic article has a smaller average connected pore diameter than porous zirconia ceramic material obtained by compacting zirconia powder, like 3Y-TZP powder from Tosoh Comp.

Due to the nano-scaled particle size and specific average connected pore diameter of the material used for producing the porous zirconia ceramic material of the porous dental ceramic article, this material has a different sintering behaviour compared to the zirconia ceramic material of dental materials which are commercially available (e.g. LAVA™ Frame from 3M ESPE) and other zirconia ceramics available on the dental market being typically produced by compacting and pressing zirconia powder (e.g. 3Y-TZP zirconia powder from Tosoh Comp.). The Vickers hardness of the material is in a particular range.

If the Vickers hardness of the material is too low, the machinability could fall off in quality (edge chipping or breaking of the workpiece) as well as in the ease of manual reworking to individualize the frame of a dental restoration or a monolithic restoration as well. If the Vickers hardness of the material is too high, the wear of the machining tools may increase in an uneconomic range or the tool could break and destroy the workpiece. The biaxial flexural strength of the material is typically also in a particular range.

It was found that if the biaxial flexural strength of the material is too low, the material tends to crack during the milling process or during the manual finishing by a dental technician. On the other hand, if the biaxial flexural strength of the material is too high, the processing of the material by a milling machine is often not possible with reasonable efforts. The milling tool used or the milled material often tend to chip or break. In such a case the shaping of the material had to be done by grinding, e.g. using a Cerec™ grinding machine (Sirona).

The material of the porous zirconia ceramic article can be characterized by at least one of the following features:
ZrO2 content: from about 70 to about 98 mol % or from about 80 to about 97 mol %;
HfO2 content: from about 0 to about 2 mol % or from about 0.1 to about 1.8 mol %;
Y2O3 content: from about 1 to about 15 mol % or from about 1.5 to about 10 mol % or from about 2 to about 5 mol %;
Al2O3 content: from about 0 to about 1 mol % or from about 0.005 to about 0.5 mol % or from about 0.01 to about 0.1 mol %.

According to a further embodiment, the porous zirconia article has a composition being characterized by the following features:
ZrO2 content: from about 90 to about 98 mol %,
HfO2 content: from about 0 to about 2 mol %,
Y2O3 content: from about 1 to about 5 mol %,
Al2O3 content: from about 0 to about 0.1 mol %.

It was found that a higher $Y_2O_3$ content typically leads to an increase of the cubic crystal phase in the zirconia ceramic material after sintering the material to final density. A higher content of the cubic crystal phase may contribute to a better translucency.

According to a particular embodiment the porous zirconia article can be characterized by the following features:
showing a N2 adsorption of isotherm type IV according to IUPAC classification,
showing a N2 adsorption with a hysteresis loop in a p/p0 range of 0.70 to 0.95,
average connected pore diameter: from about 15 to about 60,
average grain size: less than about 100 nm,
BET surface: from about 15 to about 100 m²/g or from about 16 to about 60 m²/g,
Biaxial flexural strength: from about 10 to about 40 MPa,
x, y, z dimension: at least about 5 mm,
Vickers hardness: from about 25 to about 150, and
Density: from about 40% to about 60% of theoretical density.

The zirconia ceramic dental article described herein may have an x, y, and z dimensions of at least 3 mm (in some embodiments, at least 5 mm, 10 mm, 15 mm, 20 mm, or even 25 mm) and a density of at least 98.5 (in some embodiments, 99, 99.5, 99.9, or even at least 99.99) percent of theoretical density, wherein at least 70 mole percent of the crystalline metal oxide is $ZrO_2$, and wherein the $ZrO_2$ has an average grain size less than 400 nanometers (in some embodiments, less than 300 nanometers, 200 nanometers, 150 nanometers, 100 nanometers, or even less than 80 nanometers).

Optionally, the zirconia ceramic dental article described herein may comprise at least one of $Y_2O_3$ (e.g. in a range from 1 to 15, 1 to 5, 6 to 9, 3.5 to 4.5 or even 7 to 8 mole percent of the crystalline metal oxide is $Y_2O_3$), $La_2O_3$ (e.g., up to 5 mole percent $La_2O_3$), $Al_2O_3$ (e.g., up to 0.5 mole percent $Al_2O_3$).

One exemplary zirconia ceramic dental article comprises in a range from 1 to 5 mole percent of the crystalline metal oxide is $Y_2O_3$, 0 to 2 mole percent of the crystalline metal oxide is $La_2O_3$ and in a range from 93 to 97 mole percent of the crystalline metal oxide is $ZrO_2$. This general composition has been observed to yield a combination of high biaxial flexure strength and good optical transmittance.

Another exemplary zirconia ceramic dental article comprises in a range from 6 to 9 mol % $Y_2O_3$, 0 to 2 mol % $La_2O_3$, and in a range from 89 to 94 mol % $ZrO_2$. This general composition range has been observed to yield a combination of good biaxial flexure strength and high optical transmittance.

Another exemplary zirconia ceramic dental article comprises in a range from 3.5 to 4.5 mol % $Y_2O_3$, 0 to 2 mol % $La_2O_3$, and in a range from 93.5 to 96.5 mol % $ZrO_2$. This general composition has been observed to yield a combination of especially high biaxial flexure strength and good optical transmittance.

Another exemplary zirconia ceramic dental article comprises in a range from 7 to 8 mol % $Y_2O_3$, 0 to 2 mol % $La_2O_3$, and in a range from 90 to 93 mol % $ZrO_2$. This general composition range has been observed a combination of good biaxial flexure strength and especially high optical transmittance.

The lower yttria compositions are believed to be more desirable where high strength is required and moderate optical transmittance is sufficient. The higher yttria compositions are believed to be more desirable where high optical transmittance is required and moderate strength is sufficient.

In some embodiments of the zirconia ceramic dental article, the $ZrO_2$ is all cubic $ZrO_2$. In some embodiments, the $ZrO_2$ is all tetragonal. In some embodiments, the zirconia is a mixture of tetragonal and cubic. Although not wanting to be bound by theory, based on the equilibrium phase diagram for $ZrO_2$ and $Y_2O_3$, mixtures of the cubic and tetragonal phases would be expected when the $Y_2O_3$ content is in the range from 2 to 8 mole percent and the material is sintered in the range from about 1200° C. to about 1250° C.

Embodiments with about 3.5 to 4.5 mol % $Y_2O_3$ with a mixture of tetragonal and some cubic structure exhibit an exceptional combination of strength and optical transmittance. The average grain size in one instance was 156 nm. When these materials are held at the sintering temperature for a prolonged time the grain size increased to 168 nm and the good transmittance of the material was substantially reduced. In a similar manner, if the sintering temperature was raised to about 1500° C. and held for 2 h, the grain size increased to 444 nm and the good optical transmittance was lost. It appears that maintaining the grain size of this composition below 175 nm is helpful for good optical transmission.

Embodiments containing about 7 to 8 mol % $Y_2O_3$, with a mixture of cubic and some tetragonal structure, exhibit the best transmittance, and may be particularly useful in applications where lower strength can be tolerated. This is surprising as it would be expected that compositions composed entirely of the cubic phase would exhibit the best transmission as there would be no tetragonal phase to scatter light.

The zirconia material of the porous dental ceramic article described in the present text can be obtained by a process comprising the step of heat treating or calcining a zirconia aerogel.

The zirconia aerogel can typically be characterized by at least one of the following features:

a. comprising crystalline zirconia particles having an average primary particle size in a range from 2 nm to 50 nm or from about 2 nm to about 30 nm or from about 2 to about 20 or from about 2 to about 15 nm;

b. content of crystalline zirconia particles: at least about 85 mol.-%;

c. having an organic content of at least 3 wt.-% or within a range from about 3 to about 10 wt.-%;

d. x, y, z dimension: at least about 5 or at least about 8 or at least about 10 or at least about 20 mm.

A combination of the features [(a), (b)] or [(a), (c)] or [(a), (b), (c)] or [(a), (b), (c), (d)] can be preferred. The heat treatment of the zirconia aerogel for obtaining the porous zirconia article is typically done under the following conditions:

temperature: from about 900 to about 1100° C. or from about 950 to about 1090° C.; from about 975 to about 1080° C.;

atmosphere: air or inert gas (e.g. nitrogen, argon);

duration: until a density of about 40 to about 60% of the final density of the material has been reached.

The heat treatment or calcining can be conducted in one or more steps.

In a first heat treatment step a binder burn-out could be performed to remove all organic additives from previous process steps to obtain a so called "white body".

In a second heat treatment step the strength and/or the hardness of the white-body could be adjusted to the needs of the follow up processes like machining. In case of a machinable blank the sintering protocol should reflect the interaction of temperature with strength and/or hardness. If the temperature is too low, the hardness and/or strength of the resulting article might be too low. This can cause problems during a later machining step, e.g. with respect to chipping.

If, on the other hand, the temperature is too high, the hardness and/or strength of the material may become too high. This can cause problems during a later machining step as well, e.g. with respect to the machining tool durability.

The dwell time (that is the time during which the aerogel is kept at that temperature) is helpful as well to tune strength and/or hardness to the specific needs of the chosen machining technology. The dwell time, however, can also be in a range from about 0 to about 24 h or from about 0.1 to about 5 h.

If the dwell time is too long, the dental mill blanks may become too hard to be machined under reasonable conditions.

According to one embodiment, the porous zirconia article can be obtained by a process comprising the steps of:

providing a zirconia sol comprising crystalline metal oxide particles and a solvent;

optionally concentrating the zirconia sol to provide a concentrated zirconia sol;

mixing the sol with a polymerizable organic matrix (e.g. adding a reactive surface modifier to the zirconia sol and optionally an initiator being able to polymerizable surface-modified particles of the zirconia sol);

optionally casting the zirconia sol into a mould to provide a casted zirconia sol, curing the polymerizable organic matrix of the zirconia sol to form a gel (sometimes also referred to as gelation step);

removing the solvent from the gel (e.g. by first removing water, if present, from the gel via a solvent exchange process to provide an at least partially de-watered gel;

followed by a further extraction step where the remaining solvent is extracted e.g. via super critical extraction) to provide the aerogel;

optionally cutting the aerogel into smaller pieces;

heat-treating the aerogel to obtain a machinable porous zirconia material or article.

The process of producing the porous ceramic zirconia material typically starts with providing a sol of $ZrO_2$ particles. To the sol of $ZrO_2$ particles a surface-modifying agent is added, preferably a crosslinkable surface-modifying agent (e.g. a radically reactive surface modifier). The $ZrO_2$ particles having been surface-modified with a crosslinkable agent can be polymerized, if desired, to provide a composition comprising crosslinked $ZrO_2$ particles.

The crosslinkable surface-modifying agent can be removed later, e.g. during a calcining and/or pre-sintering step.

If desired, the sol is casted into a mould. The mould may have the negative shape of the dental mill block to be provided. Due to size reduction which may be caused by heat treatments of the material, the size of the mould is typically larger than the size of the final dental mill blank. The shape of the mould is not particularly limited.

The casted zirconia sol is typically treated with heat or radiation in order to start polymerization of the reactive surface modifier. This process usually results in a gel. If present and desired, water may be removed from the gel, at least partially.

Remaining solvent of the above described sol/gel process is removed, e.g. by supercritical extraction techniques resulting in an aerogel (e.g. in block form). If desired, the aerogel may be cut into smaller pieces, e.g. having the shape of the dental mill blank.

Selectively applying the composition to the surface of the porous dental ceramic article is usually achieved by painting e.g. using a brush. However, the composition can also be applied by using a sponge or fabric or by spraying.

In order to avoid a spreading of the composition, the porous dental ceramic article should preferably not be watery or splashy wet. Drying the treated dental ceramic article is not absolutely necessary, but can be preferred to reduce the time needed for firing and to avoid undesired in-homogenous color effects. Drying can be effected by simply storing the dental ceramic article e.g. on a plate at ambient conditions for a couple of hours (about 1 to about 3 h). If, however, a high boiling solvent is used, drying might be difficult to achieve. The process of producing the zirconia ceramic dental article may further comprise the step of firing or sintering the porous zirconia dental article having been treated with the whitening composition. The firing conditions are typically dependent on the ceramic material used.

The firing usually takes place for a $ZrO_2$ based ceramic at a temperature above about 1300° C., preferably above about 1400° C., more preferably above about 1450° C. and lasts for at least about 0.5 h, preferably for at least about 1 h, more preferably for at least about 2 h. The firing will result in a zirconia ceramic dental article, sometime also referred to as crystalline metal oxide article. If conducted, the firing or sintering step should be accomplished under conditions which results in a dental ceramic article having an acceptable tooth like color (e.g. a color which fits into the Vita™ shade guide.

Useful sintering conditions can be characterized by one or more of the following parameters:

temperature: from about 900 to about 1500° C. or from about 1000 to about 1400° C. or from about 1100° C. to about 1350° C. or from about 1200° C. to about 1400° C. or from about 1300° C. to about 1400° C. or from about 1320° C. to about 1400° C. or from about 1340° C. to about 1350° C.

atmosphere: air or inert gas (e.g. nitrogen, argon);

duration: until a density of about 95 or about 98 or about 99 to about 100% of the final density of the material has been reached.

dwell time: from about 1 to about 24 h or from about 2 to about 12 h;

pressure: ambient pressure.

A furnace which can be used is the commercially available Lava™ Therm (3M ESPE).

During the firing process the porous dental ceramic article is sintered to its final shape, thereby undergoing changes with regard to dimension, density, hardness, bending strength and/or grain size.

The dwell time (that is the time during which the article is kept at that temperature) is not really critical. The dwell time can be zero. The dwell time, however, can also be in a range from about 0 to about 24 h or from about 0.1 to about 5 h.

The firing temperature and dwell time (that is, the time period during which a particular temperature is kept) are typically correlated. A higher temperature typically requires only a short dwell time. Thus, the dwell time, may last from about 0 (e.g. if the firing temperature is about 1550° C.) to about 10 h (e.g. if the firing temperature is about 1100° C.) or from about 0.1 to about 8 h.

Generally, the sintering or firing conditions are adjusted such that the sintered dental ceramic article has a density of equal or greater than about 98% compared with the theoretically achievable density.

The invention is also directed to the dental ceramic article obtainable or obtained by the process described in the present text. A dental ceramic article having being treated according to the above described process steps is different from dental ceramic articles which have been treated with essentially water-based coloring or whitening solutions. Applying water-based coloring or whitening solutions to the surface of dental ceramic articles typically leads to diffuse coloring or whitening of the whole dental ceramic article, whereas the composition described in the present text allows for a more accurate, well defined whitening effect.

If desired, the extent of diffusion of the composition on the surface of the treated dental ceramic article can be determined as follows:

The width of a line drawn with the inventive composition can be visually confirmed after sintering. More accurately, X-ray fluorescence (XRF) measurements can be conducted in micro mapping mode to determine the line's width, i.e. scanning the surface of the ceramic in e.g. 0.25 mm steps and measuring only small spots of e.g. about 0.5 mm diameter.

A width of e.g. about 0.5 mm of the drawn structures is considered to meet the expectations of a dental technician in most cases for an effect agent being applied to only selective parts of the surface of a dental ceramic. The dental ceramic article may have the shape of a crown, bridge, inlay, onlay, veneer, facing, coping, crown and bridged framework, implant, abutment, orthodontic appliances (e.g. brackets, buccal tubes, cleats and buttons) and parts thereof.

A typical process of producing a zirconia ceramic dental article comprises the steps of:

a) providing a dental mill blank comprising a porous zirconia ceramic material, b) placing the dental mill blank in a machining device, c) machining the porous zirconia ceramic material to obtain a machined porous zirconia ceramic dental article, the machined porous zirconia ceramic dental article having the shape of a crown, bridge, inlay, onlay, veneer, facing, coping, crown and bridged framework, implant, abutment, orthodontic appliances (e.g. brackets, buccal tubes, cleats and buttons) and parts thereof, d) applying the composition described in the present text to only some parts of the surface of the machined porous zirconia ceramic dental article, e) optionally drying the machined porous zirconia ceramic dental article f) optionally sintering the machined porous zirconia ceramic dental article.

The ceramic dental article after having conducted a sintering or firing step can usually be characterized by at least one or more or all of the following features:

density: fully sintered density of at least about 98.5 (in some embodiments, 99, 99.5, 99.9, or even at least 99.99) percent of theoretical density;

phase content tetragonal phase: from about 1 to about 100 wt.-% or from about 10 to about 100 wt.-%; cubic phase: from about 30 to about 100 wt.-% or from about 50 to about 90 wt.-%;

biaxial flexural strength: from about 450 MPa to about 2200 MPa, or from about 500 MPa to about 2000 MPa.

According to a further embodiment, the invention is directed to a kit of parts comprising:

at least one receptacle containing the composition as described in the present text;

one receptacle containing the liquid as described in the present text; and optionally at least one receptacle containing a coloring solution, optionally application and mixing appliances, at least one porous dental ceramic article as described in the present text.

Examples of receptacles include bottles, wells, tubes and vessels.

A typical example of a kit according to the invention includes about 2 to 10 receptacles containing a) the composition as described in the present text, b) a separate receptacle containing only the liquid contained in the composition, c) one or more receptacles containing coloring solutions each differing from the others by its content and/or concentration of coloring metal ions.

Coloring solutions for dental ceramics are meanwhile well known in the art. Examples of coloring solutions are described in U.S. Pat. No. 6,709,694, US 2006/0117989, WO 2009/014903, EP application No. 11177189. The content of these references is herewith incorporated by reference. Theses coloring liquids typically comprise water, metal cations selected from rare earth elements, transition metal and mixtures thereof, and sometimes a complexing agent or further additives like (poly)ethylene glycol. The coloring liquids are typically used for homogeneously coloring dental ceramics and in particular porous dental ceramic framework.

The liquid being provided in a separate receptacle enables the practitioner to further individualize or dilute the composition, especially with respect to its intensity. Examples of application appliances include brushes, sponges, (hollow) needles, etc. Examples of mixing appliances include mixing wells, trays, plates, slides, etc.

Neither the composition nor the porous zirconia dental article described in the present text do typically contain components which might produce a toxic, injurious, or immunological response in living tissue or components or additives which jeopardize the intended purpose to be achieved with the present invention, especially in the sintered ceramic.

Thus, for examples components or additives added in an amount which finally (e.g. after a sintering step) results in a non-tooth-colored article are usually not contained in the final dental restoration. Typically, an article is characterized as tooth colored if it can be allocated a color from the Vita™ color code system, known to the person skilled in the art.

Moreover, if possible, the composition should not or only contain a small amount of ingredients which can be detrimental to the firing equipment during the sintering process.

Additionally, components which will reduce the mechanical strength of the dental restoration to a degree, where mechanical failure will occur, are usually also not included in the dental article. According to a specific embodiment, the composition described in the present text does not contain reactive organic monomers (i.e. chemically reactive moieties like double bonds, e.g. (meth)acrylates). Thus, after preparation, the composition does not exhibit chemical reactivity under ambient conditions, i.e. components being present in the composition do not react with each other at ambient conditions. The composition does also typically not contain initiators suitable to start the curing reaction of reactive monomers.

The composition does typically also not contain filler or filler particles. Thus, particles which can be removed by filtration and/or precipitate from the composition are not contained. The zirconia ceramic dental article does usually not contain glass, glass ceramic materials, lithium disilicate ceramic materials, or combinations thereof. The producing of the zirconia material described in the present text does typically also not require the application of a hot isostatic pressing step (HIP).

The complete disclosures of the patents, patent documents, and publications cited herein are incorporated by reference in their entirety as if each were individually incorporated. The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements

Method for Measuring N2 Sorption Isotherms, BET Surface Area, Pore Volume, Average Connected Pore Diameter The samples were run on either on a QUANTACHROME AUTOSORB-1 BET Analyzer" (Quantachrome Instruments, Boynton Beach, Fla.) or a BELSORP-mini instrument (BEL Japan Inc., Osaka, Japan). The samples were weighed and outgassed at 200° C. for two days then subjected to a $N_2$ sorption process with an appropriate number and distribution of measurement points, e.g. 55 adsorb points and 20 desorb points from a $p/p_0$ range $1\times10^6$ to 1 and back to 0.05 giving full isotherms. The specific surface area S was calculated by the BET method (Details regarding calculation see Autosorb-1 Operating Manual Ver. 1.51 IV. Theory and Discussion; Quantachrome Instruments, Inc.). The total pore volume $V_{liq}$ is derived from the amount of vapor adsorbed at a relative pressure close to unity ($p/p_0$ closest to 1), by assuming that the pores are then filled with liquid adsorbate (Details regarding calculation see Autosorb-1 Operating Manual Ver. 1.51 IV. Theory and Discussion; Quantachrome Instruments, Inc.). The average pore diameter (d) is calculated from the surface area (S) and the total pore volume ($V_{liq}$):

$$d = \frac{4Vliq}{S}.$$

Average Grain Size

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Particle Size

If desired, particle size measurements can be done using a light scattering particle sizer equipped with a red laser having a 633 nm wavelength of light (obtainable under the trade designation "ZETA SIZER—Nano Series, Model ZEN3600" from Malvern Instruments Inc., Westborough, Mass.). Each sample is analyzed in a polystyrene sample cuvette. The sample cuvette is filled with a particle dispersion containing about 1 wt.-% solids. The sample cuvette is then placed in the instrument and equilibrated at 25° C. The automatic size-measurement procedure can then be run. The instrument automatically adjusts the laser-beam position and attenuator setting to obtain the best measurement of particle size.

The method of Photon Correlation Spectroscopy (PCS) is used by the software to calculate the particle size. PCS uses the fluctuating light intensity to measure Brownian motion of the particles in the liquid.

Density

If desired, the density of the pre-sintered or sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.).

To measure the density of the pre-sintered material the sample is first weighed in air (A). Then the sample is immersed in water using vacuum overnight. The immersed sample is weighed in air (B) and then weighed under water (C). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(B-C))\ \rho 0$, where $\rho 0$ is the density of water.

To measure the density of the sintered material the sample is first weighed in air (A), then immersed in water (B) The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(A-B))\ \rho 0$, where $\rho 0$ is the density of water.

The relative density can be calculated by reference to the theoretical density ($\rho t$) of the material, $\rho rel=(\rho/\rho t)100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry or wet cut saw. The diameter of the samples should be between 12 and 20 mm. Each wafer is centred on a support of three steel balls. The support diameter depends on the sample diameter and should have maximum 14 mm and should be at least 1 mm smaller than the sample diameter. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Materials Used

TABLE 1

| Material name or abbreviation | Description |
| --- | --- |
| Zirconium(IV) acetate | An aqueous solution of zirconium acetate containing nominally 16.3 wt.-% Zr obtained from Magnesium Elektron, Inc., Flemington, NJ. The aqueous solution was exposed to an ion exchange resin (obtained under the trade designation "AMBERLYTE IR 120" from Rohm and Haas Company, Philadelphia, PA) before use (oxide content 21.85 wt.-%). |
| DI water | De-ionized water |
| Yttrium(III) acetate | Yttrium (III) acetate tetrahydrate obtained from AMR Technologies Inc., Toronto, Canada (oxide content 33.4 wt.-%) |
| Lanthanum(III) oxide | Lanthanum (III) oxide obtained from Alfa Aesar, Ward Hill, MA (oxide content 99.45 wt.-%) |
| HEMA | 2-Hydroxyethyl methacrylate; Aldrich Chemical Company |
| 2,2'-Azobis(2-methylbutyronitrile), ("VAZO 67") | 2,2'-Azobis(2-methylbutyronitrile), obtained from E. I. du Pont de Nemours and Company, Wilmington, DE under the trade designation "VAZO 67" |
| Acrylic Acid | Acrylic acid obtained from Alfa Aesar, Ward Hill, MA |
| Ethanol | Ethanol 200 proof obtained from Koptec, King of Prusia, PA |
| Glycerol | Glycerol obtained from Sigma Aldrich, Germany |
| Aluminium(III) isopropoxide | Aluminium(III) isopropoxide obtained from Sigma Aldrich, Germany |
| Titanium(IV) isopropoxide | Titanium(III) isopropoxide obtained from Alfa Aesar, Germany |
| Erbium(III) acetate hydrate | Erbium(III) acetate hydrate obtained from Treibacher Industrie AG, Austria |
| Praseodymium(III) acetate hydrate | Praseodymium(III) acetate hydrate obtained from Treibacher Industrie AG, Austria |
| Manganese(II) acetate tetrahydrate | Manganese(II) acetate tetrahydrate obtained from Sigma Aldrich, Germany |
| Triammonium-citrate | Triammonium-citrate obtained from Sigma Aldrich, Germany |
| Diammonium-EDTA | Diammonium-EDTA obtained from Acros Organics, Belgium |
| PEG35000 | Polyethylene glycol (Mw 35,000) obtained from Merck, Germany |

TABLE 1-continued

| Material name or abbreviation | Description |
| --- | --- |
| Ammonia solution | Ammonia solution (25 wt.-%) obtained from Fisher Scientific, UK |

Preparation of $ZrO_2$ (88 Mol-%)/$Y_2O_3$ (12 Mol-%) Sol (Sol C1)

Sol compositions are reported in mole percent inorganic oxide. Sol C1 was prepared as follows: (All other sols were prepared by similar methods in similar equipment.)

The hydrothermal reactor was prepared from 15 meters of stainless steel braided smooth tube hose (0.64 cm inside diameter, 0.17 cm thick wall; obtained under the trade designation "DUPONT T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DUPONT T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm that was immersed in an ice-water bath to cool the material and a backpressure regulator valve was used to maintain an exit pressure of 2.76 MPa.

A precursor solution was prepared by combining the zirconium acetate solution (2.000 grams) with DI water (2205.3 grams). Yttrium acetate (327.8 grams) was added while mixing until full dissolution. The solids content of the resulting solutions was measured gravimetrically (120° C./hr. forced air oven) to be 22.16 wt.-%. D.I. water (718 grams) was added to adjust the final concentration to 19 wt.-%. This procedure was repeated three times to give a total of about 15.115 grams of precursor material. The resulting solution was pumped at a rate of 11.48 ml/min. through the hydrothermal reactor. The temperature was 225° C. and the average residence time was 42 min. A clear and stable zirconia sol was obtained.

Table 2 is a summary of the compositions prepared and the process conditions used for other sols produced in a similar manner as Sol C1.

TABLE 2

| Sol | $ZrO_2$ [mol %] | $Y_2O_3$ [mol %] | $La_2O_3$ [mol %] | Residence time [min] | Temperature [° C.] |
| --- | --- | --- | --- | --- | --- |
| T1 | 97.7 | 2.3 | 0 | 42 | 207 |
| C1 | 88 | 12 | 0 | 42 | 225 |
| C2 | 88 | 12 | 0 | 42 | 207 |
| S1 | 93.5 | 5 | 1.5 | 42 | 225 |

Sol Concentration and Diafiltration

The resulting sols were concentrated (20-35 wt.-% solids) first via ultrafiltration using a membrane cartridge (obtained under the trade designation "M21S-100-01P" from Spectrum Laboratories Inc., Rancho Dominguez, Calif.), and then via constant volume diafiltration using the same membrane cartridge. The resulting sol was then further concentrated via rotary evaporation.

Gel Preparation

The gels were prepared by combining the T and C sols to obtain the desired oxide composition and adjusting the oxide, acetic acid and solvent composition via diafiltration, distillation or a combination thereof. Sol S1 was prepared with one desired oxide composition, so that no further mixing of sols was required. Only acetic acid and solvent composition were adjusted via diafiltration, distillation or a combination thereof.

The acrylic acid, HEMA and initiator were added, the sol placed in a mold and thermally cured at 50° C. for 4 hours. A typical procedure is given for G1 below. The composition of the all the gels are given in Table 3 (the solvent is made up of water and ethanol).

Example G1

A 141.1 g sample of Sol C1 (prepared and diafiltered and concentrated as described above, 30.4 wt.-% oxide and 3.02 wt.-% acetic acid) and 400 g of Sol T1 (prepared and diafiltered and concentrated as described above, 44.2 wt.-% oxide and 2.30 wt.-% acetic acid) were charged in to a 1000 ml RB flask. Water (133.3 g) was removed via rotary evaporation resulting in viscous somewhat dry material. Ethanol (121.2 g), acrylic acid (23.13 g), HEMA (11.8 g) were added to the flask. The contents were stirred overnight resulting is a fluid translucent sol. 2,2'-azobis(2-methylbutyronitrile) ("VAZO 67") (1.2 g) was added and stirred until dissolved. The contents of the flask were then purged with $N_2$ gas for 21 min. The sample (translucent and low viscosity) was charged to cylindrical containers (29 mm diameter). Each container was about 18 ml in volume and each was sealed on both ends (very little air gap was left between the top and liquid). The samples were allowed to stand for about 1 h then placed in an oven to cure (50° C., 4 h). This resulted in a clear translucent blue gel. The gel was removed from the container and placed in a 473 ml wide mouth jar (three gels per jar). The jar was filled with ethanol (275 g, denatured). The sample was soaked for 24 h then the ethanol was replaced with fresh ethanol. The sample was soaked for 24 h then the ethanol was replaced with a third batch of fresh ethanol. The sample was allowed to soak until the supercritical extraction was done. The above manipulations were done minimizing the amount of time the gel was exposed to the air.

Table 3 is a summary of the gel production conditions used for other gels produced in a similar manner to Example G1.

TABLE 3

|  | sol(s) used | T-sol:C-sol | Oxide (wt.-%) | Acetic acid (wt.-%) | Acrylic acid (wt.-%) | Hema (wt. %) | Solvent |
|---|---|---|---|---|---|---|---|
| G-1 | T1:C1 | 75.54:24.45 | 39.33 | 3.34 | 4.14 | 2.13 | 51.06 |
| G-2 | T1:C2 | 75.51:24.48 | 39.99 | 5.92 | 4.24 | 2.17 | 46.94 |
| G-3 | T1:C2 | 60.67:39.33 | 39.80 | 6.02 | 4.24 | 2.17 | 46.98 |
| G-4 | S1 | n.a. | 40.41 | 2.36 | 4.24 | 2.17 | 50.82 |

Extraction Process

The gels were loaded into the supercritical extractor. The wet $ZrO_2$-based gels were removed separately from the ethanol bath, weighed, placed individually inside small canvas pouches, and then stored briefly in another ethanol bath before being loaded into the 10-L extractor vessel. For extraction of the gels, about 3500 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (setpoint: −12.5° C.) through a heat exchanger to heat the $CO_2$ to 60° C. and into the 10-L extractor vessel until an internal pressure of 11.0 MPa was reached. At these conditions, carbon dioxide is supercritical. Once the extractor operating conditions of 11 MPa and 60° C. were met, a PID-controlled needle valve regulated the pressure inside the extractor vessel by opening and closing to allow the extractor effluent to pass through a porous 316L stainless steel frit (obtained from Mott Corporation as Model #1100S-5.480 DIA-0.062-10-A), then through a heat exchanger to cool the effluent to 30° C., and finally into a 5-L cyclone separator vessel that was maintained at room temperature and pressure less than 5.5 MPa, where the extracted ethanol and gas-phase $CO_2$ were separated and collected throughout the extraction cycle for recycling and reuse. Supercritical carbon dioxide ($scCO_2$) was pumped continuously through the 10-L extractor vessel for 7 hours from the time the operating conditions were achieved. After the 7-hour extraction cycle, the extractor vessel was slowly vented into the cyclone separator over 16 hours from 11 MPa to atmospheric pressure at 60° C. before the lid was opened and the dried canvas pouches containing the aerogel were removed. The dry aerogels were removed from their canvas pouches, weighed, and transferred into 237 ml glass jars packed with tissue paper for storage.

Burnout/De-binder Process

The extracted aerogel samples from above were removed from their closed container and set on an aluminium oxide plate, covered with aluminium oxide cylinders and fired in air according to the following schedule in a chamber furnace ("Nabertherm 60 liter"): i—heat from 20° C. to 220° C. at 18° C./h rate; ii—heat from 220° C. to 244° C. at 1° C./h rate; iii—heat from 244° C. to 400° C. at 6° C./h rate; iv—heat from 400° C. to 900° C. at 60° C./h rate; v—hold at 900° C. for 2 h and vi—cool down from 900° C. to 20° C. at 600° C./h rate. After burnout process, the samples were crack free.

Pre-sintering Process

The de-bindered discs were set on an aluminium oxide plate and fired in air according to the following schedule in a chamber furnace (Nabertherm 1 liter): i—heat from 20° C. to 900° C. at 10° C./min. rate; ii—heat from 900° C. to 1020° C. at 2° C./min. iii—hold at 1020° C. for 2 hours and iv—cool down from 1020° C. to 600° C. in 1 h. Pre-sintering steps were finished when furnace was cooled down to room temperature.

The pre-sintered blocks were sliced into 1.6 mm thick discs and dried afterwards at 120° C. for 2 h.

Opacifying Composition

Opacifying Composition L1:

5.0 g of glycerol were mixed with 1.5 g of aluminum(III) isopropoxide and 2.4 g of triammonium citrate by stirring until a homogeneous solution was obtained.

Opacifying Composition L2:

5.00 g of glycerol were mixed with 3.00 g of titanium(IV) isopropoxide and 0.88 g of ammonia solution (25 wt.-%) by stirring until a homogeneous solution was obtained.

Application

Inventive Example 1

Composition L1 was applied with a brush to a dry disc of porous pre-sintered material G4. Half of the disc and one line were painted with the composition. The disc was sintered afterwards to full density at 1300° C. for 2 h (heating rate: 2 K/min) This procedure was repeated with a disc of porous pre-sintered material G4, that had been immersed in an experimental dental zirconia coloring liquid (containing 21.669 g de-mineralized water, 0.601 g erbium acetate, 0.081 g praseodymium acetate, 0.003 g manganese acetate, 0,647 g triammonium-citrate, 0.007 g diammonium-EDTA and 2.013 g PEG35000) for 2 min, then wiped clean with a paper cloth and allowed to dry for another 5 min before application of composition L1. As a result, two dense zirconia discs with more opaque areas where the composition had been applied were obtained.

Inventive Example 2

Composition L2 was applied with a brush to a dry disc of porous pre-sintered material G4. Half of the disc and one line were painted with the composition. The disc was sintered afterwards to full density at 1300° C. for 2 h (heating rate: 2 K/min)

This procedure was repeated with a disc of porous pre-sintered material G4, that had been immersed in the experimental coloring liquid from Inventive Example 1 for 2 min, then wiped clean with a paper cloth and allowed to dry for another 5 min before application of composition L2. As a result, two dense zirconia discs with more opaque areas where the composition had been applied were obtained.

Comparative Example 1

For the Comparative Example 1, a standard zirconia block (Lava™ Plus, 3M ESPE Dental Division; 3M Deutschland GmbH) was sliced into 2.0 mm thick discs and dried at 120° C. for 2 h. Composition L1 was applied with a brush to a dry disc of porous pre-sintered Lava™ Plus material. Half of the disc and one line were painted with the liquid. The disc was sintered afterwards following the standard protocol (1450° C. for 2 h, heating rate 10 K/min) according to the information provided by the manufacturer.

This procedure was repeated with a disc of porous pre-sintered Lava™ Plus material, that had been in the experimental coloring liquid from Inventive Example 1 for 2 min, then wiped clean with a paper cloth and allowed to dry for another 5 min before application of composition L1.

As a result, two dense zirconia discs were obtained. But the areas where the composition had been applied showed an opacifying effect that was weaker and less defined than the effect obtained according to Inventive Example 1.

Comparative Example 2

For the Comparative Example 2, a standard zirconia block (Lava™ Plus, 3M ESPE Dental Division; 3M Deutschland GmbH) was sliced into 2.0 mm thick discs and dried at 120° C. for 2 h. Composition L2 was applied with a brush to a dry disc of porous pre-sintered Lava™ Plus material. Half of the disc and one line were painted with the liquid. The disc was sintered afterwards following the standard protocol (1450° C. for 2 h, heating rate 10 K/min) according to the information provided by the manufacturer. This procedure was repeated with a disc of porous pre-sintered Lava™ Plus material, that had been immersed in the experimental coloring liquid from Inventive Example 1 for 2 min, then wiped clean with a paper cloth and allowed to dry for another 5 mins before application of composition L2.

As a result, two dense zirconia discs were obtained. But the areas where the composition had been applied showed an opacifying effect that was weaker and less defined than the effect obtained according to the Inventive Example 2.

In FIG. 1 the respective sintered zirconia discs as fired are shown: from left to right: Inventive Example 1, Comparative Example 1, Inventive Example 2, Comparative Example 2; Upper row: colored; lower row: uncolored.

The opacifying effects which can be achieved on the zirconia materials tested can be rated as follows:

| Sample | Inv. Ex. 1 Isotherm type IV Zirconia Material | Comp. Ex. 1 Isotherm type II Zirconia Material | Inv. Ex. 2 Isotherm type IV Zirconia Material | Comp. Ex 2 Isotherm type II Zirconia Material |
|---|---|---|---|---|
| Colored | ++ | −− | + | −− |
| Uncolored | ++ | − | + | − |

"++": very good;
"+": good;
"−−": very bad;
"−": bad

What is claimed is:

1. A process of treating parts of the surface of a porous dental zirconia article comprising the steps of:
    a) providing a composition and a porous zirconia article having an outer surface,
    b) applying the composition to the surface of the porous dental zirconia article,
    c) optionally drying the porous dental zirconia article, and
    d) optionally firing the porous dental zirconia article,
the composition comprising:
    liquid being miscible with water, but not being water,
    whitening agent comprising nano-sized metal oxide particles, metal ion containing components or mixtures thereof, and
    stabilizer,
the porous dental zirconia article showing a N2 adsorption and/or desorption of isotherm type IV according to IUPAC classification.

2. The process of claim 1, wherein the whitening agent comprises nano-sized particles having a diameter from about 1 nm to about 500 nm.

3. The process of claim 1, wherein the composition is essentially free of either or all of the following components:
    filler,
    coloring ions selected from iron, erbium, manganese, praseodymium or mixtures thereof,
    reactive organic monomers,
    initiators suitable for curing reactive monomers,
    and combinations thereof.

4. The process of claim 1, wherein the metal cations or nano-sized metal oxide particles of the whitening agent comprises Al, Ti, Zr and mixtures thereof.

5. The process of claim 1, wherein the liquid is selected from the group consisting of polyol(s), glycol ether(s), glycerol ether(s), alcohol(s) and mixtures thereof.

6. The process of claim 1, wherein the composition is characterized by at least one or all of the following features:
viscosity: from about 10 mPa*s to about 10,000 mPas*s at 23° C.,
being transparent to visible light.

7. The process of claim 1, wherein the composition comprises as stabilizer acid, base, complexing agent or a mixture thereof, preferably selected from the group consisting of acetylacetonate, crown ethers, cryptands, ethylenediaminetriacetate and its salts, ethylenediaminetetraacetate (EDTA) and its salts, nitrilotriacetate (NTA) and its salts, citric acid and its salts, triethylentetramine, porphin, poly acrylate, poly asparagate, acidic peptides, phthalocyanin, salicylate, glycinate, lactate, propylendiamine, ascorbate, oxalic acid and its salts, acetic acid and its salts ammonia and its salts and mixtures thereof.

8. The process of claim 1, the composition comprising:
a) the liquid in an amount of about 20 to about 98 wt.-%;
b) the metal oxide or metal ion containing components of the whitening agent in an amount of about 1 to about 20 wt.-%, calculated as wt.-% of the metal with respect to the whole composition;
c) the stabilizer in an amount of about 1 to about 75 wt.-%; and
d) additives in an amount of about 0 to about 10 wt.-%;
wt.-% with respect to the whole composition.

9. The process of claim 1, the porous dental zirconia article being characterized by at least one of the following features:
showing a nitrogen adsorption and desorption isotherm with hysteresis loop;
showing a hysteresis loop of type H1 according to IUPAC classification;
showing a $N_2$ adsorption and desorption isotherm with a hysteresis loop in a $p/p_0$ range of 0.70 to 0.95;
average connected pore diameter: from about 10 to about 100 nm;
average grain size: less than about 100 nm;
BET surface: from about 10 to about 200 $m^2/g$;
biaxial flexural strength: from about 10 to about 40;
Vickers hardness: from about 25 to about 150;
density: about 30 to about 95% of theoretical density;
x, y, z dimension: at least about 5 mm;
having an isotropic shrinkage behaviour.

10. The process of claim 1, the porous dental zirconia article being characterized by at least one of the following features:
i) the porous dental zirconia article being in a pre-sintered stage before the composition is applied,
ii) the porous dental zirconia article being wet before the composition is applied.

11. The process of claim 1, the process comprising the steps of;
a) providing a composition and a porous zirconia article having an outer surface;
b) applying the composition to only a part of the outer surface of the porous dental zirconia article;
c) optionally drying the porous dental zirconia article; and
d) optionally firing the porous dental zirconia article;
wherein the composition comprises:
a liquid being miscible with water, but not being water;
the liquid being present in an amount of about 20 to about 98 wt.-%;
the liquid being selected from the group consisting of polyol(s), glycol ether(s), glycerol ether(s), alcohol(s) and mixtures thereof;
a whitening agent comprising nano-sized metal oxide particles, metal ion containing components or mixtures thereof;
the metal oxide or metal ion containing components of the whitening agent being present in an amount of about 1 to about 20 wt.-%, calculated as wt.-% of the metal with respect to the whole composition;
the metal cations or metal oxide particles of the whitening agent comprising ions of Al, Ti, Zr and mixtures thereof; and
a stabilizer being selected from acid, base, complexing agent or mixture thereof in an amount of about 1 to about 75 wt.-%;
wt.-% with respect to the whole composition;
the composition being further characterized by the following features:
viscosity: from about 10 mPa*s to about 10,000 mPas*s at 23° C.;
wherein the composition being essentially free of the following components:
filler;
coloring ions selected from iron, erbium, manganese, praseodymium or mixtures thereof;
reactive organic monomers;
wherein the porous dental zirconia article is characterized by the following features:
showing a N2 adsorption of isotherm type IV according to IUPAC classification;
showing a N2 adsorption with a hysteresis loop in a p/p0 range of 0.70 to 0.95;
average connected pore diameter: from about 15 to about 60 nm;
average grain size: less than about 100 nm;
BET surface: from about 15 to about 100 $m^2/g$ or from about 16 to about 60 $m^2/g$;
Biaxial flexural strength: from about 10 to about 40 MPa;
x, y, z dimension: at least about 5 mm;
Density: from about 40% to about 60% of theoretical density;
ZrO2 content: from about 90 to about 98 mol %;
HfO2 content: from about 0 to about 2 mol %;
Y2O3 content: from about 1 to about 5 mol %; and
Al2O3 content: from about 0 to about 0.1 mol %;
wherein the optional firing step being conducted under the following conditions:
temperature: from about 1200° C. to about 1400° C.;
atmosphere: air or inert gas;
duration: until a density of at least about 95 or at least about 98 of the final density of the material has been reached;
dwell time: from about 1 to about 24 h; and
pressure: ambient pressure.

12. A dental zirconia article obtainable by the process of claim 1, the dental zirconia article having the shape of a crown, bridge, inlay, onlay, veneer, facing, coping, crown or bridged framework, implant, abutment, orthodontic appliances and parts thereof.

13. A composition to be applied on the surface of a porous dental zirconia article, the composition comprising;
a liquid being miscible with water, but not being water;
a whitening agent comprising nano-sized metal oxide particles, metal ion containing components or mixtures thereof;
a stabilizer, preferably acid, base, complexing agent or mixture thereof;
the porous dental zirconia article of claim 1.

14. Kit of parts comprising
at least one receptacle containing the composition of claim 1;
at least one receptacle containing a coloring liquid;
optionally a receptacle containing the liquid contained in the composition;
optionally application and mixing appliances; and
at least one porous dental zirconia article of claim 1.

15. Use of a composition of claim 1 for whitening only parts of the surface of a porous dental zirconia article of claim 1.

* * * * *

UNITED STATES PATENT AND TRADEMARK OFFICE
CERTIFICATE OF CORRECTION

PATENT NO.        : 9,655,817 B2
APPLICATION NO.   : 14/646277
DATED             : May 23, 2017
INVENTOR(S)       : Michael Jahns It is certified that error appears in the above-identified patent and that said Letters Patent is hereby corrected as shown below:

On the Title Page

Item [57]
Line 12, delete "the" and insert -- The --, therefor.

In the Specification

Column 4
Line 61, after "7 mm)" insert -- . --.

Column 9
Line 23, after "text" insert -- . --.

Column 12
Line 22, after "5" insert -- . --.

Column 14
Lines 54-55, delete "triethylentetramine;" and insert -- triethylenetriamine; --, therefor.

Column 14
Line 55, delete "phthalocyanin$^2$ bis(salicilate)" and insert -- phthalocyanin$^{2-}$ bis(salicylate) --, therefor.

Column 14
Line 62, delete "(COO)$_2^2$." and insert -- (COO)$_2^{2-}$. --, therefor.

Column 15
Line 14, delete "anti oxidant" and insert -- antioxidant --, therefor.

Column 15
Line 49, after "wt.-%" insert -- . --.

Signed and Sealed this
Sixteenth Day of January, 2018

Joseph Matal
*Performing the Functions and Duties of the*
*Under Secretary of Commerce for Intellectual Property and*
*Director of the United States Patent and Trademark Office*

Column 17
Line 42, after "machining)" insert -- . --.

Column 18
Line 14, delete "(HV 1)." and insert -- (HV 1); --, therefor.

Column 18
Line 16, delete "20 mm;" and insert -- 20 mm. --, therefor.

Column 21
Line 61, delete "sol," and insert -- sol; --, therefor.

Column 23
Line 7, delete "reached." and insert -- reached; --, therefor.

Column 24
Line 12, after "article" insert -- , --.

Column 27
Line 38, delete ""AMBERLYTE" and insert -- "AMBERLITE --, therefor.

Column 27
Line 43, approx., delete "Lathanum" and insert -- Lanthanum --, therefor.

Column 27
Line 52, delete "Prusia," and insert -- Prussia, --, therefor.

Column 31,
Line 31, after "K/min)" insert -- . --.

In the Claims

Column 33
Line 3, Claim 6, delete "mPas*s" and insert -- mPa*s --, therefor.

Column 33
Line 12, Claim 7, delete "triethylentetramine," and insert -- triethylenetriamine, --, therefor.

Column 34
Line 17, Claim 11, delete "mPas*s" and insert -- mPa*s --, therefor.